United States Patent
Elsik

(10) Patent No.: US 10,123,532 B2
(45) Date of Patent: Nov. 13, 2018

(54) SPRAY DRIFT REDUCTION AGENTS COMPRISING LOW HYDROPHILIC-LIPOPHILIC BALANCE SURFACTANTS

(71) Applicant: Huntsman Petrochemical LLC, The Woodlands, TX (US)

(72) Inventor: Curtis M. Elsik, The Woodlands, TX (US)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 10 days.

(21) Appl. No.: 14/987,126

(22) Filed: Jan. 4, 2016

(65) Prior Publication Data

US 2016/0219873 A1    Aug. 4, 2016

Related U.S. Application Data

(62) Division of application No. 13/696,826, filed as application No. PCT/US2012/032265 on Apr. 5, 2012, now abandoned.

(60) Provisional application No. 61/477,251, filed on Apr. 20, 2011.

(51) Int. Cl.
  *A01N 25/24* (2006.01)
  *A01N 25/30* (2006.01)
  *A01N 57/12* (2006.01)

(52) U.S. Cl.
  CPC .............. *A01N 25/24* (2013.01); *A01N 25/30* (2013.01); *A01N 57/12* (2013.01)

(58) Field of Classification Search
  CPC ......... A01N 25/24; A01N 25/30; A01N 57/20
  See application file for complete search history.

(56) References Cited

U.S. PATENT DOCUMENTS

| | | | |
|---|---|---|---|
| 5,352,672 A | 10/1994 | Staetz et al. | |
| 5,529,975 A | 6/1996 | Chamberlain | |
| 5,612,285 A * | 3/1997 | Arnold | A01N 57/20 504/206 |
| 6,165,939 A * | 12/2000 | Agbaje | A01N 25/04 504/105 |
| 6,214,771 B1 | 4/2001 | Dexter | |
| 6,251,415 B1 | 6/2001 | Herbert | |
| 6,797,673 B1 | 9/2004 | Worthley et al. | |
| 7,776,790 B2 * | 8/2010 | Herold | A01N 25/02 504/206 |
| 8,129,312 B2 | 3/2012 | Berghaus et al. | |
| 8,247,350 B2 | 8/2012 | Ogawa et al. | |
| 8,993,629 B2 | 3/2015 | Sun | |
| 2002/0183206 A1 | 12/2002 | Jimoh | |
| 2003/0096726 A1 * | 5/2003 | Smith | C11D 1/65 510/424 |
| 2003/0125211 A1 | 7/2003 | Woznica et al. | |
| 2003/0153461 A1 | 8/2003 | Parrish et al. | |
| 2003/0191026 A1 | 10/2003 | Killick et al. | |
| 2005/0037933 A1 | 2/2005 | Bingeman | |
| 2005/0043182 A1 * | 2/2005 | Douglass | A01N 25/02 504/363 |
| 2005/0043218 A1 | 2/2005 | Tsyrlova et al. | |
| 2006/0057173 A1 | 3/2006 | Sims | |
| 2006/0063678 A1 | 3/2006 | Wright et al. | |
| 2006/0154826 A1 | 7/2006 | Bernardini et al. | |
| 2006/0180677 A1 | 8/2006 | McManic et al. | |
| 2006/0270556 A1 | 11/2006 | Wright et al. | |
| 2007/0137042 A1 | 6/2007 | Focht et al. | |
| 2008/0020933 A1 | 1/2008 | Tann et al. | |
| 2009/0215626 A1 | 8/2009 | Elsik et al. | |
| 2009/0270258 A1 | 10/2009 | Rose et al. | |
| 2009/0306003 A1 | 12/2009 | Kabanov et al. | |
| 2010/0105559 A1 | 4/2010 | Elsik et al. | |
| 2010/0113275 A1 | 5/2010 | Qin et al. | |
| 2010/0152048 A1 | 6/2010 | Rose et al. | |
| 2012/0040831 A1 | 2/2012 | Tann et al. | |

FOREIGN PATENT DOCUMENTS

| | | |
|---|---|---|
| CN | 1038568 A | 1/1990 |
| CN | 101267733 A | 9/2008 |
| CN | 101636087 A | 1/2010 |
| CN | 101731223 A | 6/2010 |
| EP | 0 331 474 A | 9/1989 |
| EP | 0 331 474 A1 | 9/1989 |
| GB | 2107987 | 5/1983 |
| GB | 2107987 A | 5/1983 |
| GB | 2306965 A | 5/1997 |
| JP | 09137065 | 5/1997 |
| JP | 2005-527596 A | 9/2005 |
| WO | 91/14365 A | 10/1991 |
| WO | 9114365 A1 | 10/1991 |
| WO | 92/03047 A | 3/1992 |
| WO | 9203047 | 5/1992 |
| WO | 02/098221 A | 12/2002 |

(Continued)

OTHER PUBLICATIONS

McKenzie, "Nonionic Surfactants", Jan. 1978, J. Am. Oil Chemists' Soc., vol. 55, pp. 93-97.*
"Performance Products: Metalworking Chemicals, Product Information", Jan. 1, 2005, pp. 1-54, XP55131807; URL: http://www.huntsman.com/performance_products/Media Library/.
Morjan, et al., "Fungicidal Effects of Glyphosate and Glyphosate Formulations on Four Species of Entomopathogenic Fungi", 2002, Environmental Entomology, vol. 31 iss. 6, pp. 1206-1212.
Office Action and Search Report for Chinese Application No. 201280013357.2 dated Oct. 8, 2014.
Office Action for U.S. Appl. No. 13/696,826 dated Oct. 10, 2013.
Final Office Action for U.S. Appl. No. 13/696,826 dated Feb. 26, 2014.
Office Action for U.S. Appl. No. 13/696,826 dated Jan. 26, 2015.
Final Office Action for U.S. Appl. No. 13/696,826 dated Sep. 2, 2015.

(Continued)

*Primary Examiner* — Ali Soroush
(74) *Attorney, Agent, or Firm* — Huntsman Petrochemical LLC; Edward Korompai

(57) ABSTRACT

Embodiments of the present invention disclose using low hydrophilic-lipophilic balance surfactants as spray drift reduction agents and methods of using such agents.

3 Claims, No Drawings

(56) References Cited

FOREIGN PATENT DOCUMENTS

| WO | 02098221 A1 | 12/2002 |
| WO | 03/096807 A | 11/2003 |
| WO | 03096807 A1 | 11/2003 |
| WO | WO-2008/045850 A2 * | 4/2008 |
| WO | 2008/111482 A | 9/2008 |
| WO | 2010/026127 A | 3/2010 |
| WO | 2010026127 | 3/2010 |
| WO | 2010/051435 A | 5/2010 |
| WO | 2010051435 | 5/2010 |
| WO | 2010/124151 A | 10/2010 |
| WO | 2010124151 A1 | 10/2010 |

OTHER PUBLICATIONS

Morjan et al., "Fungicidal Effects of Glyphosate and Glyphosate Formulations on Four Species of Entomopathogenic Fungi", 2002, Enviromental Entomology, vol. 31 iss. 6, pp. 1206-1212.

Office Action for Japanese Application No. 2014-506438 dated Nov. 4, 2015.

A Manual of Surfactants (with attached partial English translation); Sangyo Tosho K.K.; The Fifth Print on pp. 318 to 323, II. Basic Properties of the Surfactants 7.6; Effects of the HLB Value; dated 1966; 7 total pages.

English translation of the Japanese Final Rejection for Application No. 2014-506438; dated May 11, 2016; 4 total pages.

Office Action for Japanese Application 2016-173434 dated May 17, 2017.

* cited by examiner

SPRAY DRIFT REDUCTION AGENTS COMPRISING LOW HYDROPHILIC-LIPOPHILIC BALANCE SURFACTANTS

CROSS-REFERENCE TO RELATED APPLICATIONS

This application is a divisional of U.S. patent application Ser. No. 13/696,826, filed Nov. 8, 2012, which is the national stage entry of international Application Serial No. PCT/US2012/032265, filed Apr. 5, 2012, which claims the benefit of U.S. Provisional Patent Application Ser. No. 61/477,251, filed Apr. 20, 2011. The above-referenced patent applications are herein incorporated by reference in their entirety.

FIELD OF INVENTION

This invention relates generally to drift reduction agents for use in agricultural applications, but may also be applied in other applications where it is beneficial to reduce off-target deposition.

BACKGROUND

Spray drift may be defined as the physical movement of airborne spray particles through the air at the time of application or soon thereafter to any off-target site. In the agricultural context, formulations with greater spray drift characteristics are typically unfavorable because less of the formulation interacts with the target site. To counteract spray drift, drift reduction agents are typically added to the spray mixtures to reduce the amount of spray drift that occurs.

There are many drift reduction technology (DRT) tank mix adjuvants (TMA) currently on the market today. They can be lumped into broad categories based on their individual chemistries. There are natural polymers such as guar gum and other polysaccharides. There are synthetic polymers such as the polyacrylamides. These both function to increase extensional or kinematic viscosity, and this increased viscosity usually results in increased particle size and reduced fines. Reducing fines generally reduces spray drift. However, the polymer systems tend to increase the average particle size and broaden the particle size distribution (PSD). Bioefficacy can be adversely affected when mean particle size becomes too wide.

There are also oil products available that can be mineral or natural based, such as esterified seed oil. These oils produce either emulsions or invert emulsions that are thought to function by preventing small drops from forming during spray generation due to the emulsion phase present.

Surfactants are typically added to many pesticidal spray solutions to increase bioefficacy. When a surfactant is added to a spray solution the surface tension and dynamic surface tensions may be reduced. It is thought that this reduction in surface tension makes it easier to generate smaller droplets. Adding a surfactant typically reduces the average particle size and more importantly generally increases the amount of fines generated during spraying. It is the finer particles that typically drift the most. Therefore, despite their other benefits, surfactants are not typically thought of as agents to reduce spray drift.

DETAILED DESCRIPTION OF INVENTION

Surprisingly, it has been discovered that relatively low hydrophilic-lipophilic balance (HLB) surfactants may be used as spray drift reduction agents. Such surfactants generally reduce the amount of fines generated during spraying. Rather, other surfactants usually increase the amount of fines when added to the spray tank since the reduced tension makes it easier for the spray drops to break up.

Surfactants are amphiphilic molecules that concentrate at the interface between two phases and modify the properties of that interface. A list of surfactants can be found in McCutcheon's Emulsifiers & Detergents or the Industrial Surfactants Handbook. The hydrophilic-lipophilic balance (HLB) of a surfactant is measured on an empirical scale developed by Griffin (W. C. Griffin, J. Cosmet. Chem., 1, 311, 1949). This scale ranges from 0 to 20, with 0 for a completely lipophilic molecule and 20 for a completely hydrophilic molecule. The function of surfactants can be generally described by their HLB number. Defoaming surfactants have an HLB range of 1-3. Water-in-oil emulsifiers have an HLB range of 3-6. Wetting agents have an HLB range of 7-9. Oil-in-water emulsifiers have an HLB range of 8-18. Detergents have an HLB range of 13-15. Solubilizers have an HLB range of 15-18.

Surfactants with low HLB are not considered soluble in water. They are considered dispersible in water. They may form this dispersed phase spontaneously, without agitation. In other words, low HLB surfactants form a surfactant-rich dispersed phase when added to water. The presence of the dispersed surfactant-rich phase is thought to reduce the amount of fines formed during the spray atomization process. This novel DRT TMA chemistry is not believed to deleteriously broaden the particle size distribution as the polymeric DRT agents do.

For this application, "low HLB" is defined as any surfactant HLB that will result in the surfactant's cloud point as measured in the targeted spray system being below the temperature at which the system is sprayed. In some embodiments this HLB is from about 7 to about 9. However, the actual HLB required will therefore be a function of the spray system components and their concentrations. When spraying at temperatures above the surfactant cloud point, a dispersed surfactant-rich phase will form, and this dispersed phase will function to reduce the fines generated even though the surface tension is reduced due to the presence of the dispersed surfactant phase. Higher HLB surfactants should also reduce fines if used above their cloud point. This would normally required elevated temperatures in the absence of formulation additives designed to reduce the cloud point.

Examples of the low HLB surfactants of the current invention may include, but are not limited to, alcohol alkoxylates, alkylamine alkoxylates, polyetheramine alkoxylates, ethylene oxide/propylene oxide block polymers, phosphate esters, alkyl sulfates, alkyl ether sulfates, alkyl and alkylbenzene sulfonates, fatty acid esters, fatty oil alkoxylates, saccharide derivatives, sorbitan derivatives, alkyl phenol alkoxylates, arylphenol alkoxylates, sulphosuccinates and sulphosuccinamates and combinations thereof. The surfactants can be nonionic, anionic, cationic or zwitterionic.

Commercial examples of such low HLB surfactants include the SURFONIC® surfactants that are commercially available from the Huntsman Corporation of The Woodlands, Tex. SURFONIC® L12-3 surfactant is a linear C10-12 alcohol ethoxylate with an average 3 moles ethylene oxide (EO) and an HLB=9.0. SURFONIC® L24-3 surfactant is a linear C12-16 alcohol ethoxylate with an average 3 moles ethylene oxide (EO) and an HLB=8.0. SURFONIC® TDA-3B surfactant is a branched C13 alcohol ethoxylate with an average 3 moles ethylene oxide (EO) and an HLB=8.0. SURFONIC® DA-4 surfactant is a branched C10 alcohol ethoxylate with an average 4 moles ethylene oxide (EO) and an HLB=10.5. SURFONIC® CO-15 surfactant is a castor oil ethoxylate with an average 15 moles ethylene oxide (EO) and an HLB=8.2. SURFONIC® N-60 surfactant is a nonylphenol ethoxylate with an average of 6 moles EO and an HLB=10.9. SURFONIC® T-5 surfactant is a tallowamine ethoxylate with an average of 5 moles EO and an HLB=9.0.

Embodiments of the present invention also disclose a pesticidal composition to reduce spray drift that comprises one or more active ingredients and one or more low hydrophilic-lipophilic balance surfactants. In embodiments, the one or more active ingredients may be herbicides, insecticides, fungicides or combinations thereof. Such herbicides may be water soluble herbicides or other herbicides such as 2,4-D esters. In another embodiment, the one or more active ingredients may be glyphosate or one or more salts or esters thereof.

Embodiments of the present invention disclose a method of reducing spray drift by providing a composition for spraying that comprises a pesticide and a low hydrophilic-lipophilic balance surfactant and spraying the composition.

Further embodiments include a method of controlling weeds by contacting such a pesticidal composition to the weed or soil; a method of controlling insects by applying such a pesticidal composition to insects, soils or crops; and a method of controlling fungi by applying such a pesticidal composition to the fungi, crops or soils.

Embodiments of the present invention disclose a method of reducing spray drift comprising providing a composition for spraying that comprises a surfactant and spraying the spray mixture above the surfactant's cloud point as measured in the spray mixture.

Embodiments of the present invention disclose a spray composition comprising a blend of two or more surfactants wherein the blend has a low hydrophilic-lipophilic balance.

To further illustrate various illustrative embodiments of the present invention, the following examples are provided.

EXAMPLES

Table 1 shows particle size data. The spray particle size distribution and percent fines can be measured using ASTM Standard Test Method E2798: "Characterization of Performance of Pesticide Spray Drift Reduction Adjuvants for Ground Application." Sample solutions where sprayed through a nozzle (XR8004VS) at 40 psig.

Example 1, the pesticide composition, contains 1.7 v/v % POWERMAX® herbicide (commercially available from The Monsanto Company of St. Louis, Mo. POWERMAX is a registered mark of The Monsanto Company) diluted into 342 ppm hardness water. Example 2 is the same base composition as Example 1 except it also contains 0.5 v/v % SURFONIC® L24-3 surfactant which is commercially available from Huntsman Corporation of The Woodlands, Tex. SURFONIC® L24-3 surfactant is a linear C12-16 alcohol ethoxylate with an average 3 moles ethylene oxide (EO) and an HLB=8.0. Example 3 is the same base composition as Example 1 except it also contains 0.5% SURFONIC® L12-3 surfactant which is commercially available from the Huntsman Corporation of The Woodlands, Tex. SURFONIC L12-3 surfactant is a linear C10-12 alcohol ethoxylate with an average 3 moles ethylene oxide (EO) and an HLB=9.0. Example 4 is the same base composition as Example 1 except it also contains 0.5% SURFONIC® TDA-3B surfactant which is commercially available from Huntsman Corporation of The Woodlands, Tex. SURFONIC TDA-3B surfactant is a branched C13 alcohol ethoxylate with an average 3 moles ethylene oxide (EO) and an HLB=8.0. Example 5 is the same base composition as Example 1 except it also contains 0.5% TERMIX® 5910 tank mix adjuvant which is commercially available from Huntsman Corporation of The Woodlands, Tex.

TABLE 1

Particle Size Data

| Example | % FINES < 105 μm | D10 (μm) | VMD [D50] (μm) | D90 (μm) | REL SPAN | KINE VISC (cSt) | DST @ 10 mS (mN/m) | DST @ 1 s (mN/m) | EXT VISC |
|---|---|---|---|---|---|---|---|---|---|
| 1 | 16.0 | 85.7 | 198.6 | 387.9 | 1.52 | 0.734 | 51.3 | 42.9 | 1.00 |
| 2 | 10.8 | 100.0 | 265.4 | 420.9 | 1.21 | 0.844 | 52.5 | 32.1 | 6.94 |
| 3 | 9.4 | 107.5 | 238.2 | 404.6 | 1.25 | 0.870 | 36.6 | 27.5 | 6.93 |
| 4 | 8.7 | 112.5 | 273.4 | 426.7 | 1.15 | 0.827 | 48.8 | 26.9 | 6.84 |
| 5 | 9.8 | 105.8 | 251.8 | 412.5 | 1.22 | 0.743 | 43.4 | 29.7 | 6.80 |

In other embodiments of the present invention, a method is disclosed of producing a spray drift reduction composition by blending a low HLB surfactant with a second surfactant (such as higher HLB surfactants) to produce a blend with a low hydrophilic-lipophilic balance. In order to counteract the usual deleterious spray drift effects of higher HLB surfactants, a user may add low HLB surfactants to a spray tank mixture. Here the pesticidal composition would have a blend of two or more surfactants where the effective surfactant blend has a combined low HLB level.

The primary application of this technology will be to reduce drift during the spraying of pesticide formulations. However, the technology may also be applicable in other areas such as polyurethane or polyurea spraying, paint spraying, or other spraying systems where it is beneficial to reduce off-target deposition.

Table 1 shows several low HLB surfactants that reduce the amount of fines while also reducing both dynamic (10 mSec) and static (1 s) surface tension. Table 1 also shows that the low HLB surfactant SURFONIC TDA-3B reduced % fines <105 microns from 16.0 v/v % with no DRT adjuvant to a value of only 8.7%. This is almost a 50% reduction in fines, while dynamic surface tension dropped from 51.3 to 48.8 mN/m and static surface tension dropped from 42.9 to 26.9 mN/m. Normally a reduction in tension would result in an increase in the volume of fines generated during spraying.

Although the present invention and its advantages have been described in detail, it should be understood that various changes, substitutions and alterations may be made herein without departing from the spirit and scope of the invention as defined by the appended claims.

The invention claimed is:

1. A method of reducing spray drift, comprising:
adding one or more low hydrophilic-lipophilic balance ("HLB") surfactants to a pesticidal composition, wherein the pesticidal composition, comprises:
glyphosate or one or more salts or esters thereof; and water,
wherein the one or more low HLB surfactants form a surfactant-rich dispersed phase in the water, wherein the one or more low HLB surfactants are insoluble in the water, wherein the one or more low HLB surfactants is selected from the group consisting of: a linear C10-12 alcohol ethoxylate with an average 3 moles ethylene oxide (EO) and an HLB of 9.0, a linear C12-16 alcohol ethoxylate with an average 3 moles EO and an HLB of 8.0, a branched C13 alcohol ethoxylate with an average 3 moles EO and an HLB of 8.0, a branched C10 alcohol ethoxylate with an average 4 moles EO and an HLB of 10.5, a castor oil ethoxylate with an average 15 moles EO and an HLB of 8.2, and a nonylphenol ethoxylate with an average of 6 moles EO and an HLB of 10.9; and
spraying the pesticidal composition at a temperature above a cloud point temperature of the one or more low HLB surfactants, wherein the surfactant-rich dispersed phase reduces an amount of fine particles formed during the spraying.

2. The method of claim 1, wherein the one or more low HLB surfactants is a branched C13 alcohol ethoxylate with an average 3 moles EO and an HLB of 8.0.

3. The method of claim 1, wherein the pesticidal composition includes 0.5 v/v % of the one or more low HLB surfactants.

* * * * *